(12) United States Patent  (10) Patent No.: US 8,436,629 B2
Chambon  (45) Date of Patent: May 7, 2013

(54) DEVICE FOR THE CAPACITIVE MEASUREMENT OF THE QUALITY AND/OR DETERIORATION OF A FLUID, INCLUDING A CAPACITIVE SENSOR THAT IS MECHANICALLY UNCOUPLED FROM THE ELEMENT IN WHICH IT IS ENCAPSULATED

(75) Inventor: Gérald Chambon, Lausanne (CH)

(73) Assignee: Alpsens Technologies Inc., Ecublens (CH)

( * ) Notice: Subject to any disclaimer, the term of this patent is extended or adjusted under 35 U.S.C. 154(b) by 553 days.

(21) Appl. No.: 12/602,070

(22) PCT Filed: Apr. 18, 2008

(86) PCT No.: PCT/EP2008/054745
§ 371 (c)(1),
(2), (4) Date: Mar. 30, 2010

(87) PCT Pub. No.: WO2008/135367
PCT Pub. Date: Nov. 13, 2008

(65) Prior Publication Data
US 2010/0176819 A1    Jul. 15, 2010

(30) Foreign Application Priority Data

Apr. 20, 2007  (CH) ...................................... 0653/07

(51) Int. Cl.
*G01R 27/26* (2006.01)
*G01R 31/08* (2006.01)

(52) U.S. Cl.
USPC ............................ 324/686; 324/663; 324/519

(58) Field of Classification Search .................. 324/663, 324/686, 519
See application file for complete search history.

(56) References Cited

U.S. PATENT DOCUMENTS

| 6,469,521 | B1 | 10/2002 | Klun et al. |
| 6,777,009 | B1 | 8/2004 | Shealy |
| 6,822,461 | B2 * | 11/2004 | Klun ............................. 324/698 |
| 7,504,836 | B2 * | 3/2009 | Chambon et al. ............. 324/698 |
| 2006/0288877 | A1 | 12/2006 | Chambon et al. |

FOREIGN PATENT DOCUMENTS

| EP | 1 393 664 | 3/2004 |
| EP | 1 588 158 B1 | 3/2007 |
| JP | 61-44339 | 3/1986 |
| WO | 2004/065957 A1 | 8/2004 |
| WO | 2005/098406 A1 | 10/2005 |

OTHER PUBLICATIONS

Testo, "Cooking Oil Tester with Display and Alarm," from http://www.appleonehk.com/265_E.pdf, Feb. 2004, pp. 1-2.
International Search Report issued in corresponding application No. PCT/EP2008/054745, completed Jul. 16, 2008 and mailed Aug. 5, 2008.

* cited by examiner

*Primary Examiner* — Amy He
(74) *Attorney, Agent, or Firm* — Griffin & Szipl, P.C.

(57) ABSTRACT

The invention concerns a device for the capacitive measurement of the quality and/or deterioration of a fluid, wherein the device includes a sensor encapsulated in a perforated case, wherein the sensor is connected to the encapsulation so as to be mechanically uncoupled therefrom.

7 Claims, 2 Drawing Sheets

DEVICE FOR THE CAPACITIVE MEASUREMENT OF THE QUALITY AND/OR DETERIORATION OF A FLUID, INCLUDING A CAPACITIVE SENSOR THAT IS MECHANICALLY UNCOUPLED FROM THE ELEMENT IN WHICH IT IS ENCAPSULATED

This is a National Phase Application in the United States of International Patent Application No. PCT/EP2008/054745 filed Apr. 18, 2008, which claims priority on Swiss Patent Application No. 00653/07, filed Apr. 20, 2007. The entire disclosures of the above patent applications are hereby incorporated by reference.

FIELD OF THE INVENTION

The present invention concerns a device for the capacitive measurement of the quality and/or deterioration of a fluid, in particular an oil. The invention particularly concerns a device of this type that has a capacitive sensor for measuring the quality and/or deterioration of cooking oil, which is arranged directly in the cooking apparatus, and wherein the capacitive sensor, which is encapsulated in a protective case fixed in a submerged area of the vat of the cooking apparatus, is mechanically uncoupled from the element in which it is encapsulated.

BACKGROUND OF THE INVENTION

It is well know that edible oils deteriorate during cooking, particularly when they are repeatedly heated to high temperatures. These oils are typically heated to temperatures of the order of 180° C. to fry food. A multitude of chemical reactions occur at these temperatures, such as polymerisation, thermo-oxidation, etc., which significantly alter the quality of the oil. The quantity of some products of these reactions must not exceed a threshold imposed by legislation, since the oil is deemed unfit for consumption beyond the threshold. It is thus important to be able to detect the threshold in a reliable manner, so that the oil is replaced as soon as it becomes necessary. For a long time, it was left to cooks to judge, after a visual and/or olfactory inspection, whether the oil was still fit for consumption. Of course, that method is entirely subjective and is consequently unreliable.

EP Patent No, 1 588 158, which corresponds to U.S. Patent Application Publication No. US 2006/0288877 A1, discloses a device for the capacitive measurement of the quality and/or deterioration of a cooking oil to overcome these drawbacks. The content of EP Patent No, 1 588 158 and corresponding U.S. Patent Application Publication No. US 2006/0288877 A1 is incorporated herein by reference. In this device, the capacitive sensor is directly arranged in the vat of the cooking apparatus, with the sensor encapsulated in a perforated protective case, secured in a submerged area of the vat.

Although the device disclosed in that Patent Application operates satisfactorily, performing a capacitance measurement inside a deep fat fryer remains a highly delicate operation. Indeed, a variation of a few picofarads between the new oil and used oil, greatly influenced by temperature, water and impurities, is not easy to detect. Added to this is the fact that the device has to operate in a very harsh environment in which the capacitive sensor, and, possibly, the temperature sensor associated therewith, are subjected to temperatures higher than 200° C., and to shocks when careless operators strike the sensor with the baskets holding food for frying.

Protection of the capacitive sensor, and possibly, the temperature sensor associated therewith, thus constitutes an extremely important problem that needs to be addressed to avoid deterioration in measurement accuracy and/or reducing the life time of the measuring device, since the measurements are directly dependent thereon.

SUMMARY OF THE INVENTION

It is thus an object of the invention to overcome this problem by providing a device for the capacitive measurement of the quality and/or deterioration of an oil that includes a sensor, encapsulated in a perforated case, wherein the sensor is connected to the case so that it is mechanically uncoupled therefrom.

The invention mainly concerns the separation between the assembled and precisely aligned, capacitive sensor, which is relatively fragile, and the case in which it is encapsulated. The function of the case is to protect the sensor as far as possible in the following situations:

In oil, in normal use: to protect against impact from the baskets, while still allowing the oil to flow in an optimum manner, and against shocks due to any other instrument.

Outside the vat: protection against falls, shocks in the dishwasher, transport, . . . .

The mechanical uncoupling of the sensor and its encapsulating case increases the level of reliability (fewer parts under stress), extends the lifetime of the sensor and simplifies assembly. Another advantage lies in the separation of the measuring and encapsulating functions, which thus means that:

one part of the system (encapsulation) can be subcontracted yet control of the sensor assembly process is maintained.

alterations can be made to one of the parts without affecting the other.

most of the encapsulation parts can be simplified, significantly reducing constraints thereon and hence, obviously, costs:

materials: thermal stability and mechanical stress at lower temperatures lower machining tolerances, since alignment does not have to be optimal.

Thus, in accordance with a first non-limiting illustrative embodiment of the present invention, a device for the capacitive measurement of the quality and/or deterioration of a fluid is provided, wherein the device includes a sensor encapsulated in a perforated case, wherein the sensor is connected to the encapsulating case so that it is mechanically uncoupled therefrom. In accordance with a second non-limiting illustrative embodiment of the present invention, the first non-limiting embodiment is modified so that the mechanical uncoupling between the sensor and its encapsulating case is achieved by means of two strip springs that also fulfil the function of electrical contact between the sensor electrodes and contact elements of the sensor that will connect the sensor to the exterior. In accordance with a third non-limiting illustrative embodiment of the present invention, the second non-limiting embodiment is further modified so that the contact elements take the form of elastic clamps. In accordance with a fourth non-limiting, illustrative embodiment of the present invention, the second and third non-limiting embodiments are further modified so that the strip springs ensuring the mechanical separation between the sensor and its encapsulating case are made of stainless steel and have a thickness of the order of 100 microns.

BRIEF DESCRIPTION OF THE DRAWINGS

Other features and advantages of the present invention will appear more clearly in the following description of a preferred embodiment of a measuring device according to the invention, given by way of non-limiting example, with reference to the annexed drawings, in which.

DETAILED DESCRIPTION OF THE ILLUSTRATIVE EMBODIMENTS

Figure 1:
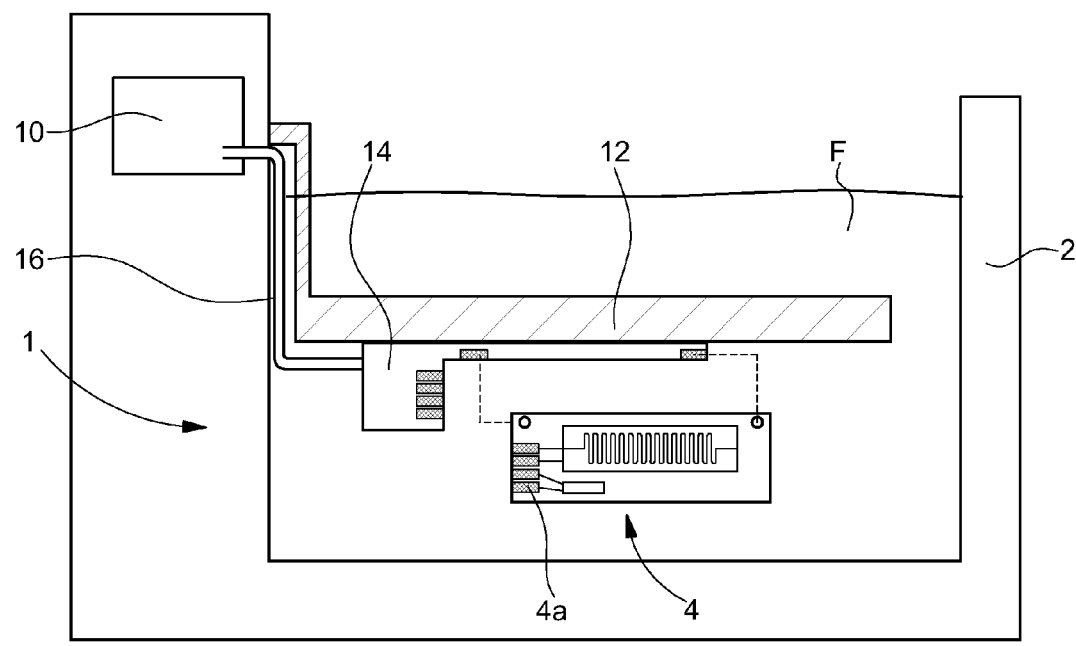
FIG. 1 is a schematic cross-section of the vat of a deep fat fryer, in which a measuring device with its encapsulated sensor according to the invention can be mounted.

Referring first of all to FIG. 1, an embodiment of a device for the capacitive measurement of the quality and/or deterioration of a fluid, particularly oil, is shown, designated by the general reference 1.

It will be noted that the following description will concern an application of a device 1 for measuring the quality and/or deterioration of an edible oil or similar, used for frying food in a cooking apparatus that has a vat 2 in which the oil can be heated, typically up to around 200° C.

Figure 2:
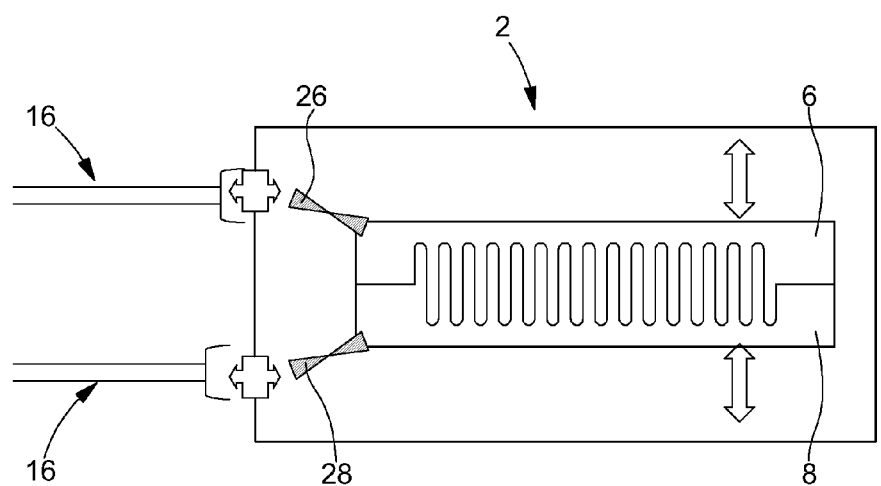
FIG. 2 is a schematic view of the encapsulated sensor of the device according to the invention.
Figure 3:
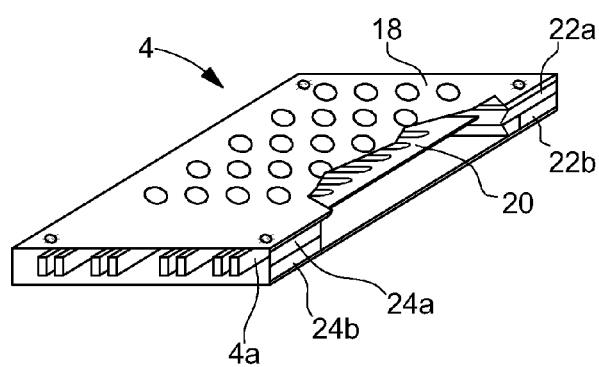
FIG. 3 is a schematic, partially torn away, perspective view of the encapsulated sensor of the device according to the invention.
Figure 4:
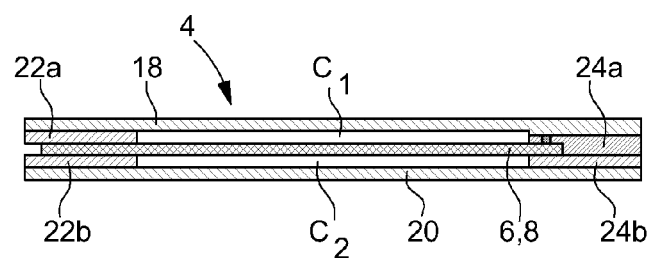
FIG. 4 is a schematic cross-section of the encapsulated sensor according to the invention.
Figure 5:
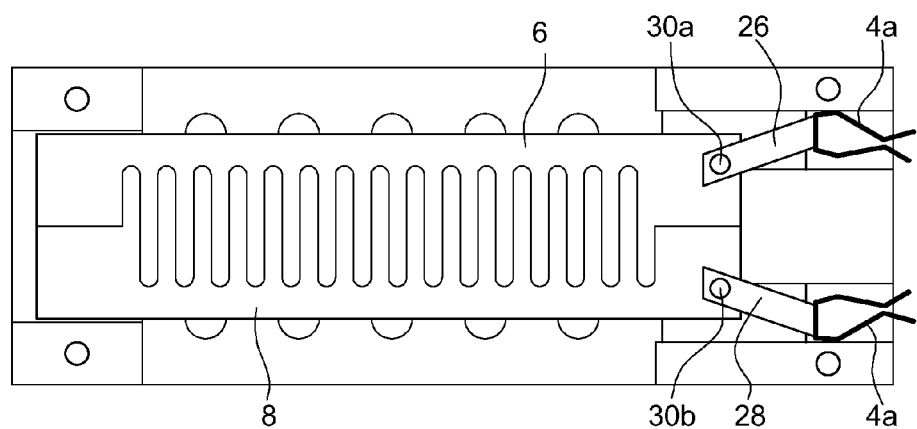
FIG. 5 is a schematic elevation of the sensor according to the invention in which one encapsulation plate has been omitted.

Measuring device 1 has an encapsulated sensor 4 including a pair of electrodes 6, 8, which are spaced apart from each other and will be submerged in a fluid F (FIG. 2), for example the oil of a deep fat fryer, whose quality and/or deterioration one wishes to measure, in order to determine whether it is still fit for use. With oil F, electrodes 6, 8 form a capacitive measuring element EFM, whose capacitance varies as a function of the dielectric constant of the oil. When the oil deteriorates, the quantity of polar components present therein increases and causes an increase in the dielectric constant thereof. Thus, by measuring the evolution of the capacitance of capacitive measuring element EFM, one can determine the degree of quality and/or deterioration of the oil. Sensor 4, and more specifically its capacitive element EFM, is thus capable of providing an electrical output signal representative of the dielectric constant of the oil across a broad temperature range, in particular between 20° C. and 200° C. An electronic processing circuit 10, arranged outside vat 2, processes the electrical signal. Sensor 4 is connected to the electronic processing circuit by electric contacts 4a. The sensor is, for example, secured in a removable manner underneath heating body 12, via a securing and connecting support 14 integral therewith. Typically, sensor 4 can be plugged into support 14 via its electric contacts 4, which may, for example, take the form of elastic clamps. The securing and connecting support 14 is connected to the electronic circuit by means of cables 16 which are protected, for example in tubes.

Each electrode 6, 8 of the pair takes the form of a comb with a plurality of teeth 6a, 8a, which are approximately parallel to each other and extend from a base 6b, 8b. Electrodes 6, 8 are arranged in relation to each other such that the teeth 6a of one electrode 6 fit between the teeth 8a of the other electrode 8. The teeth of electrodes 6 and 8 are thus arranged in approximately the same plane.

It will be noted in this regard that electrodes 6 and 8 are, for example, formed from the same flat plate cut in a suitable manner, with the plate being sufficiently rigid for the electrodes to keep their shape when they are handled. In the example described, the electrodes are made from a plate of steel used for food (low carbon austenitic 18-10 stainless steel) with a thickness of between 0.1 and 3 mm. Other types of steel used for food may also be used, for example Z7CN18-09, Z3CND18-12-02, Z6CNDT17-12 and Z7CNU16-04. The plate is cut using a laser beam, which can make air gaps between the teeth of the electrodes of between 10 nm and 1 mm. It is clear that, the smaller the air gap, the greater the sensitivity of the capacitive element. According to a variant, one could also envisage making electrodes formed of a substrate coated with a conductive material, for example a substrate coated with a layer of gold, platinum or suchlike.

Electrodes 6 and 8 are arranged in a perforated encapsulating case. This case is formed of flat, perforated, metal plates 18, 29 between which electrodes 6 and 8 extend, with two pairs of spacers 22a, 22b and 24a, 24b made of insulating material inserted at the ends, between which electrodes 6, 8, which form the impedimetric sensor, are sandwiched. Electrodes 6, 8 are secured to plates 18, 20 via spacers 22a, 22b at one end and are guided freely between spacers 24a, 24b at their other end.

The perforations in plates 18, 20 of the encapsulating case are arranged opposite the measuring area of electrodes 6 and 8, i.e. opposite air gaps defined by the spaces between teeth 6a of electrode 6 and teeth 8a of electrode 8. Owing to this configuration, the fluid to be measured, in this case oil, bathes the other two faces of electrodes 6 and 8 on either side of the plane of the electrodes such that it can flow in proximity to teeth 6a and 8a of electrodes 6 and 8.

This electrode encapsulation structure optimises the flow of oil around the two faces of the flat electrodes and, in particular creates two channels C1, C2, respectively defined between a first surface of electrodes 6, 8 and the perforated plate 18 and a second surface of electrodes 6, 8, opposite the first surface, and perforated plate 20.

Electrodes 6 and 8 are secured to the spacers by elastic means, namely two strip springs 26, 28, which also fulfil the function of electric contact between the electrodes and contact elements 4a of sensor 2.

Mechanical uncoupling of the sensor from its encapsulating case is achieved via this elastic securing method. The strips, cut, via electro-erosion, into a stainless steel sheet that is 100 microns thick, position the sensor elastically in the encapsulating case. The sensor is guided in a perpendicular direction to the plane of plates 18 and 20 by securing elements 30a, 30b, which are housed in bores in spacers 24a, 24b. A small amount of play is left so that the sensor is "free" in the perpendicular direction to the plane of plates 18 and 20 in its position, simply resting on the insulating parts.

The spacers are preferably made of a material that is resistant to temperatures of between 20° C. and 200° C. and has a low thermal expansion coefficient, such as a ceramic material. However, they can be made of any other insulating material compatible with the application envisaged for the measuring device. By way of example, for a food-related application that has to be stable within the aforementioned temperature range, the spacers could also be made of a fluoride polymer such as Teflon.

The invention claimed is:

1. A device for capacitive measurement of a quality, or deterioration, or both the quality and deterioration, of a fluid, wherein the device includes:
   (a) a sensor comprising a pair of electrodes spaced apart from each other and arranged approximately in a same plane, wherein the sensor is encapsulated in a perforated case so that when the encapsulated sensor is immerged in the fluid, each electrode comes into contact with the fluid, and wherein the case comprises a plurality of perforated plates between which the pair of electrodes extend, with interposition of a pair of first spacers inserted at a first longitudinal end of the perforated plates and of a pair of second spacers inserted at a second longitudinal end of the one perforated plate to the first longitudinal end and between which the pair of electrodes is sandwiched, wherein the pair of electrodes is secured elastically to the plurality of perforated plates via the first spacers at the first longitudinal end, and wherein the pair of electrodes is guided freely between the second spacers at the second longitudinal end so that the sensor is attached to the perforated case so that the sensor is not rigidly mechanically coupled to the perforated case.

2. The device according to claim 1, further comprising:
(b) two strip springs disposed between the pair of electrodes and contact elements of the sensor that connect the sensor to an exterior of the device, wherein the two strip springs electrically connect the pair of electrodes to the contact elements and the two strip springs secure the sensor elastically to the perforated case that encapsulates the sensor.

3. The device according to claim 2, wherein the contact elements are elastic clamps.

4. The device according to claim 3, wherein the two strip springs ensure mechanical decoupling between the sensor and the perforated case encapsulating the sensor, and the two strip springs are made of stainless steel and have a thickness of the order of 100 microns.

5. The device according to claim 2, wherein the two strip springs ensure mechanical decoupling between the sensor and the perforated case encapsulating the sensor, and the two strip springs are made of stainless steel and have a thickness of the order of 100 microns.

6. The device according to claim 1, wherein the first spacers and the second spacers are made of a ceramic material, or a second material that is resistant to temperatures of between 20° C. and 200° C. and that has a thermal expansion coefficient that is the same as the ceramic material.

7. The device according to claim 1, wherein the first spacers and the second spacers are made of a fluoride polymer.

* * * * *